United States Patent [19]

Stulberg et al.

[11] Patent Number: 4,615,516

[45] Date of Patent: Oct. 7, 1986

[54] SPLINT FOR SURGICAL OPERATIONS ON THE KNEE

[75] Inventors: S. David Stulberg, Chicago, Ill.; Bernard Legrand, Geneva, Switzerland

[73] Assignee: Sodem Diffusion S.A., Geneva, Switzerland

[21] Appl. No.: 776,667

[22] Filed: Sep. 16, 1985

[51] Int. Cl.[4] .................... A61F 5/84

[52] U.S. Cl. .................... 269/328; 128/80 R

[58] Field of Search .................... 128/80 C, 80 H, 153, 128/80 R, 87 R; 269/328; 5/443, 444

[56] References Cited

U.S. PATENT DOCUMENTS

| | | | |
|---|---|---|---|
| 2,375,225 | 5/1945 | Herbert | 5/444 |
| 3,753,557 | 8/1973 | Kelley | 269/328 |
| 4,136,858 | 1/1979 | Peterson | 269/328 |

OTHER PUBLICATIONS

Peabody Splint Literature, Orthopedic Equipment Co., The Journal of Bone and Joint Surgery, Jul. 1952, p. 38.
*The Alvarado Knee Support,* brochure; 4 pages not dated.
*Iclinix;* brochure; 2 pp., 1984.

*Primary Examiner*—Sheldon J. Richter
*Attorney, Agent, or Firm*—Sandler & Greenblum

[57] ABSTRACT

The splint for surgical operations on the knee comprises a member for holding the ankle and the foot, immobilizing the leg in a folded position in a substantially vertical plane, and a fastening means connecting the holding member to a stand enabling the splint to be rested on the operating table. The splint is articulated about a substantially horizontal pin permitting the holding member to rock in a vertical plane is fixed on the stand by means of a longitudinal slide groove made on the stand along the axis of projection of the leg. The slide groove allows travel and positioning of the fastening means. The stand located in the sterile region fits in a support rendered integral with the operating table and the fastening means comprises a substantially vertical pivot allowing lateral deflection of the holding member.

6 Claims, 3 Drawing Figures

SPLINT FOR SURGICAL OPERATIONS ON THE KNEE

BACKGROUND OF THE INVENTION

The present invention relates to a splint for surgical operations on the knee, in particular for total prosthesis. It enables the joint to be held securely in position while enabling it to be offset causing it to gape and to facilitate intervention by the surgeon.

Various splints used in knee surgery are known, in particular the one sold under the trade mark Alvarado by the company Zimmer Inc. Another example is the splint sold by the applicants under the name Inclinix.

If reference is made to the first mentioned example, it will be found that the splint is not held correctly since it is able to move laterally and backwards. Moreover, the leg is held strictly in its plane of flexion and it is not possible to cause the joint to gape laterally. Finally, the position of the foot, inducing the degree of flexion of the leg, is controlled in a relatively crude manner in a rack.

BRIEF SUMMARY OF THE INVENTION

The precise object of the invention is to overcome these drawbacks and the invention proposes a splint of the type described above, that is a splint comprising a member for holding the ankle and the foot while immobilising the leg in a folded position in a substantially vertical plane and a fastening means connecting the holding member to a stand enabling the splint to rest on the operating table. The fastening means is articulated about a substantially horizontal axis which allows the holding member to swing in a vertical plane on the one hand and is fixed on the stand by means of a longitudinal slide groove formed on the stand along the axis of projection of the leg on the other hand. The slide groove enables the fastening means to be moved and positioned.

The improvement made resides in the fact that the stand fits into a support which is made integral with the operating table and in that the fastening means comprises a substantially vertical pivot allowing lateral deflection of the holding member.

The slide groove advantageously has on its upper face fine teeth cooperating with a member for blocking the fastening means in position. The blocking member comprises, on its lower face, teeth corresponding to those of the slide groove as well as locking means. Some elastic means release the blocking member of the slide groove when the locking means are in the unlocked position.

Unlike the support, the splint stand is in the sterile operating region. A piece of linen interposed between the stand and the support contributes towards bacterial isolation and sterility.

The support is preferably rendered integral with the operating table by a linkage which is fixed on the rails normally running along the operating table.

The pivot also preferably comprises a member for locking it in position in order to maintain the joint in a given gaping position if desired by the surgeon.

The invention will be better understood by reference to the accompanying drawings given as non-limiting examples.

DETAILED DESCRIPTION

Figure 1:
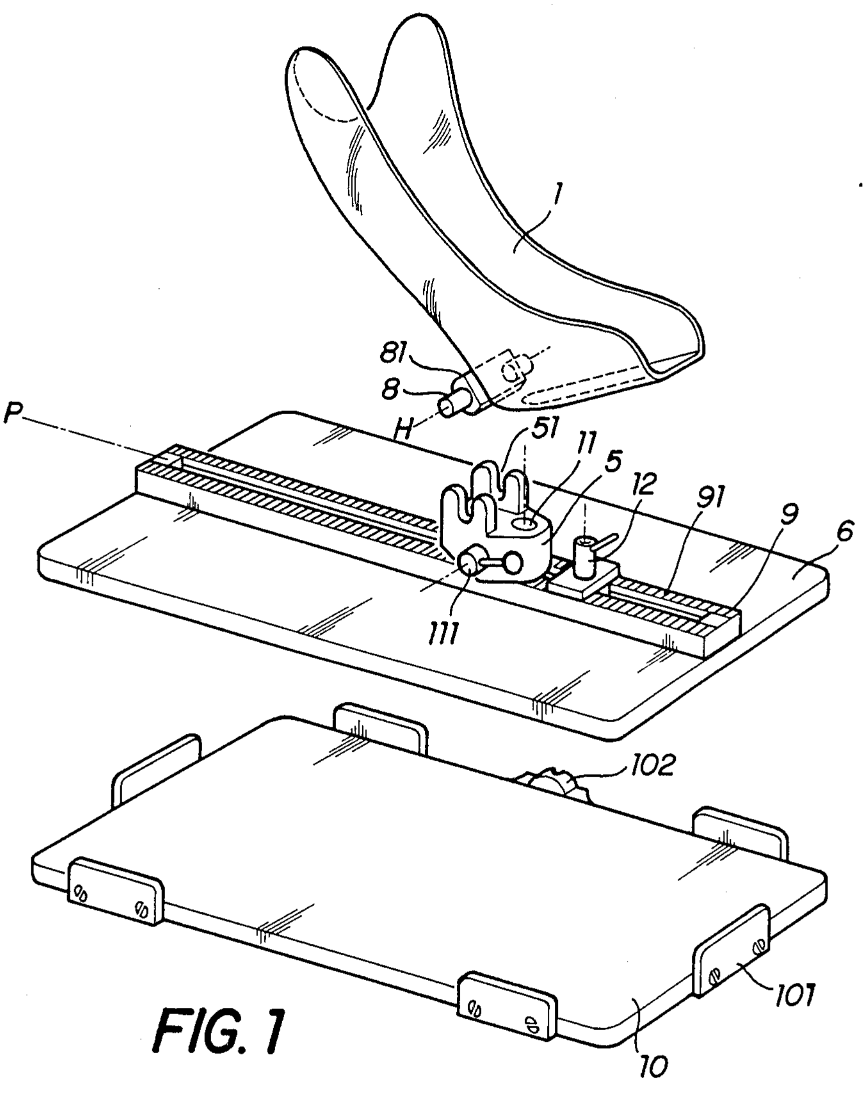
FIG. 1 is a superimposed exploded view of the splint according to the invention.

As shown in FIG. 1, which is an exploded view, the splint is composed of a holding member 1 surrounding the ankle and the foot so as to hold the leg securely. This holding member 1 comprises a pin 8 substantially along the horizontal H, which is accommodated on a fastening means 5 in two parallel grooves 51 provided for the purpose and extending from the fastening means 5. The pin 8 is fixed to the holding member 1 by a connecting element 81, which substantially has the same width as the interval between the two grooves 51. The member 1 is thus held on the fastening means 5 substantially without clearance.

The fastening means 5 is positioned in a slide groove 9 formed in a stand 6 so as to be able to travel longitudinally in the plane P which is a projection of the plane of the leg on the stand 6.

The slide groove 9 has teeth 91 on its upper face, and a member 12 for blocking the fastening means 5 enables the fastening means 5 to be immobilised in any predetermined position.

Moreover, the fastening means 5 comprises a substantially vertical pivot 11 provided with a locking member 111 according to the selected angular position.

Furthermore, the stand 6 is positioned in a support 10 having raised edges 101 for holding the stand 6 without sliding, a slight clearance merely being provided between the stand 6 and the support 10. The dimensions of the stand 6 are therefore very slightly smaller than the distance between the raised edges 101 of the support 10.

Figure 2:
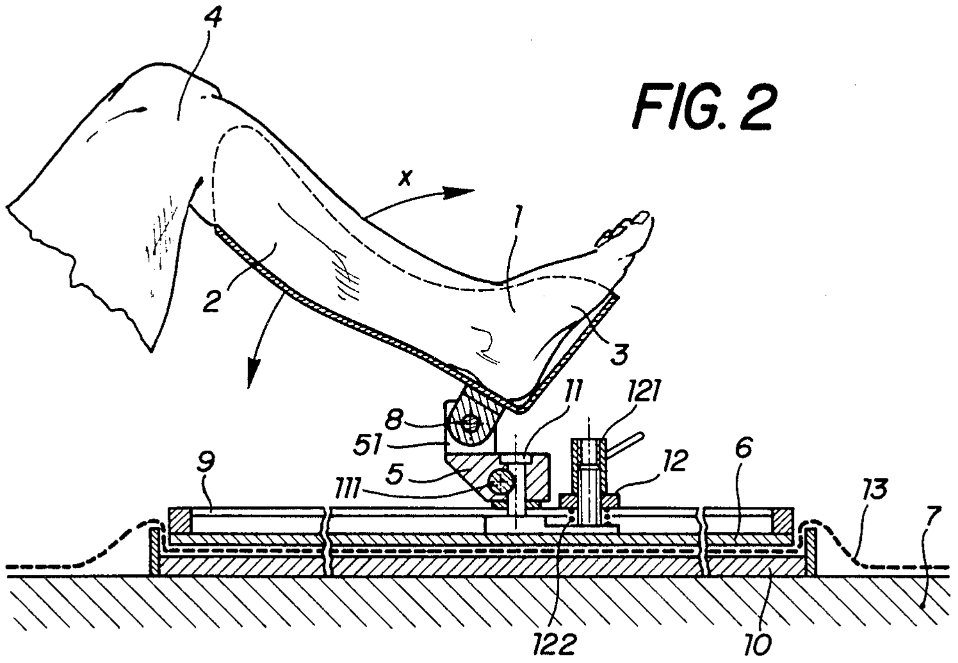
FIG. 2 is a sectional view along the axis P which is the axis of projection of the leg on the stand.

Passing onto FIG. 2, which is a sectional view along the vertical plane V passing through P, the elements described above are found together with the patient's leg 4, the ankle 2 and the foot 3 being securely held in the holding member 1. The pin 8 enables the holding member 1 to rock in the plane of the leg along x, while the fastening means 5 is able to travel along the slide groove 9 and to be locked in position by the blocking member 12 of which the lower face also comprises teeth.

The two toothed regions of the blocking member 12 and the slide groove 9 fit in one another and are blocked without being able to slide via locking means 121. A spring 122 is placed beneath the locking means 121 so as to push the locking means back up when they are in the unlocked position. As a result, the surgeon can easily slide the member 12 along the slide groove 9.

During the surgical operation, the patient's ankle 2 and foot 3 are fixed firmly on the holding member 1 by bandages (not shown).

As also shown in FIG. 2, the fastening means 5 is provided with a vertical pivot 11 which can be held and locked in position by a locking member 111.

This Figure finally shows a piece of linen 13 which is interposed between the stand 6 and the operating table 7 and therefore keeps the operating region sterile.

Figure 3:
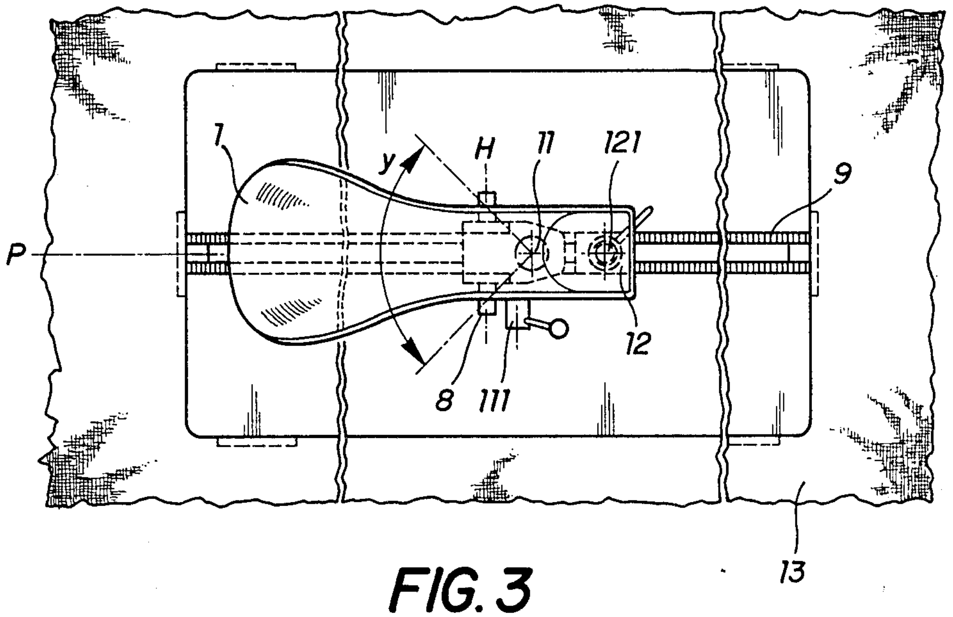
FIG. 3 is a plan view of this splint.

FIG. 3 shows all the elements just described, and it can be noted that the holding member 1 can rotate about the pivot 11 along y. It is thus possible to create a lateral deflection which will offset the leg and cause the knee joint to gape.

As shown in FIG. 1, the support 10 is fixed to the operating table 7 by means 102 on which there is positioned a linkage system which is fixed on the rails generally running round the operating table.

The significant progress made by the splint according to the invention, which enables the knee joint to be offset to facilitate the surgeon's work will easily be understood from the foregoing. Obviously, it is still possible to control the angle of bending of the knee joint by acting on the position of the fastening means 5 in the slide groove 9, which relates to the angle x about the pin 8.

What we claim is:

1. A splint for surgical operations on the knee of the type comprising a member for holding the ankle and the foot, immobilising the leg in a folded position in a substantially vertical plane, and a fastening means connecting the holding member to a stand enabling the splint to be rested on the operating table, the fastening means being articulated about a substantially horizontal pin enabling the holding member to rock in the vertical plane, on the one hand, and being fixed on the stand by means of a longitudinal slide groove formed on the stand along the axis of projection of the leg and allowing travel and positioning of the fastening means, on the other hand, wherein the stand fits in a support integral with the operating table and wherein the fastening means comprises a substantially vertical pivot allowing lateral deflection of the holding member.

2. A splint according to claim 1, wherein the slide groove has on its upper face fine teeth cooperating with a member for blocking the fastening means in position.

3. A splint according to claim 2, wherein the blocking member comprises on its lower face teeth corresponding to those of the slide groove and locking means, and elastic means releasing the member for blocking the slide groove when the locking means are in the unlocked position.

4. A splint according to claim 1, wherein unlike the support, the stand is in the sterile operating region.

5. A splint according to claim 1, wherein the support is rendered integral with the operating table by means of a linkage which is fixed on the rails running along the operating table.

6. A splint according to claim 1, wherein the pivot comprises a member for locking it in position.

* * * * *